US006230056B1

(12) United States Patent
Kroll

(10) Patent No.: US 6,230,056 B1
(45) Date of Patent: May 8, 2001

(54) METHOD AND APPARATUS FOR PREVENTING CLOTTING DURING A TRIAL FIBRILLATION

(75) Inventor: Kai Kroll, Minneapolis, MN (US)

(73) Assignee: Galvani, Ltd., Minneapolis, MN (US)

( * ) Notice: Subject to any disclaimer, the term of this patent is extended or adjusted under 35 U.S.C. 154(b) by 0 days.

(21) Appl. No.: 09/393,443

(22) Filed: Sep. 8, 1999

Related U.S. Application Data

(63) Continuation-in-part of application No. 08/931,233, filed on Sep. 15, 1997, now Pat. No. 5,925,066, and a continuation-in-part of application No. 08/754,712, filed on Dec. 6, 1996, now Pat. No. 5,978,203, which is a continuation of application No. 08/543,001, filed on Oct. 13, 1995, now abandoned, which is a continuation of application No. 08/251,349, filed on May 31, 1994, now abandoned, said application No. 08/931,233, is a continuation of application No. 08/549,982, filed on Oct. 26, 1995, now abandoned.

(60) Provisional application No. 60/099,398, filed on Sep. 8, 1998.

(51) Int. Cl.$^7$ .................................................. A61N 1/362
(52) U.S. Cl. ..................................................................... 607/9
(58) Field of Search ................................... 607/4, 5, 6, 14

(56) References Cited

U.S. PATENT DOCUMENTS

| | | | |
|---|---|---|---|
| 4,986,270 | * | 1/1991 | Cohen ......................................... 607/4 |
| 5,464,434 | * | 11/1995 | Alt ............................................... 607/6 |
| 5,601,611 | * | 2/1997 | Fayram et al. ............................. 607/6 |
| 5,913,879 | * | 6/1999 | Ferek-Petric et al. .................. 607/14 |

OTHER PUBLICATIONS

DeBehnke, Daniel, "Resuscitation time limits in experimental pulseless electrical activity cardiac arrest using cardiopulmonary bypass," *Resuscitation 27*, pp 221–229, Feb. 28, 1994.

Bleske, et al., "Comparison of adrenergic agonists for the treatment of ventricular fibrillation and pulseless electrical activity," *Resuscitation 28*, pp 239–251, Aug. 1994.

Quinn, et al., "Need for Sedation in a Patient Undergoing Active Compression—Decompression Cardiopulmonary Resuscitation," *Academic Emergency Medicine*, vol. 1, No. 5, pp. 463–467, Sep./Oct. 1994.

* cited by examiner

*Primary Examiner*—William E. Kamm
(74) *Attorney, Agent, or Firm*—Fredrikson & Byron, P.A.

(57) ABSTRACT

A device for preventing clotting during atrial fibrillation includes optional electrical cardiac output forcing (ECOF) or ICD/AED back up. The device includes a power supply for operating the device and for providing the necessary output forcing signals. The power supply is located in a housing which may be implantable into a human patient. In one embodiment, the housing acts as an electrode. At least one additional electrode is connected to the housing and may be inserted into the human heart. A ventricular lead is mounted to the electrode along with an atrial lead. The housing also contains an electrical cardiac stimulator. When a certain cardiac event, such as atrial fibrillation, is detected, anti-clotting pulses are applied to the heart via the atrial lead. If and when ventricular fibrillation is detected, further pulses of a different voltage level are applied to the heart via the ventricular lead. In one embodiment, the anti-clotting pulses are synchronized to the R-wave sensed by the ventricular lead.

32 Claims, 5 Drawing Sheets

METHOD AND APPARATUS FOR PREVENTING CLOTTING DURING A TRIAL FIBRILLATION

REFERENCE TO RELATED APPLICATIONS

This application is based on U.S. Provisional Application Serial No. 60/099,398, filed Sep. 8, 1998, and entitled ANTI-CLOTTING ATRIAL FIBRILLATION DEVICE, the contents of which are herein incorporated by reference and to which priority under 35 U.S.C. § 119 is claimed. This application is also a continuation-in-part of U.S. patent application Ser. No. 08/754,712, filed Dec. 6, 1996, now U.S. Pat. No. 5,978,203, which is a continuation of U.S. patent application Ser. No. 08/543,001, filed Oct. 13, 1995, now abandoned, which was a continuation of U.S. patent application Ser. No. 08/251,349, filed May 31, 1994, now abandoned. This application is also a continuation-in-part of U.S. patent application Ser. No.: 08/931,233, filed Sep. 15, 1997, now U.S. Pat. No. 5,925,066, which is a continuation of U.S. patent application Ser. No. 08/549,982, filed Oct. 26, 1995, now abandoned.

BACKGROUND OF THE INVENTION

1. Field of the Invention

This invention generally relates to cardiac arrhythmia treatment. In particular, the present invention relates to an implantable device for preventing clotting during atrial fibrillation.

2. Description of Related Art

Atrial fibrillation is probably the most common cardiac arrhythmia. While atrial fibrillation is not acutely life threatening, it is a major cause of hospitalization. Atrial fibrillation causes a lack of blood output from the atria which may lead to blood clots in the atria due to areas of stagnant blood flow. These blood clots may break loose and can then lodge in either the lungs, if they come from the right atrium, or in the brain causing a stroke or death if they come from the left atrium. In addition, patients afflicted with atrial fibrillation generally experience palpitations of the heart and may experience dizziness or even loss of consciousness. It is estimated that approximately fifteen percent of all elderly people experience atrial fibrillation.

Various types of oral drugs have been tried to treat atrial fibrillation. While some patients are helped by only drug therapies, the majority of patients are not successfully and safely treated with drugs and require a different type of treatment. One of the most significant shortcomings of these drugs is the side effects they may have on the patients. Specifically, in some patients, administration of these drugs leads to ventricular fibrillation which is almost always immediately fatal.

Unfortunately, atrial fibrillation may often be corrected only by a discharge of electrical energy to the heart. This type of treatment is generally referred to as cardioversion. There are many known external devices for applying cardioversion shocks to control atrial fibrillation. For example, U.S. Pat. Nos. 4,572,191 and 3,952,750 disclose a stand-by electrical shock device for atrial fibrillation. The external shocks are typically very painful and, unfortunately, often result in temporary relief for patients, sometimes lasting only a few weeks. Additionally, recently issued U.S. Pat. Nos. 5,282,837; 5,265,600; and 5,391,185 disclose various embodiments relating to implantable electrical atrial defibrillators.

Use of an electrical shock to stop atrial fibrillation poses some hitherto unresolved problems. Primarily, electrical atrial defibrillation requires shocks in the order of 1–2 Joules of electrical energy. Patients are typically conscious during atrial fibrillation and shocks of the magnitude of 1–2 Joules are very painful to the patient and are thus undesirable. Another significant disadvantage of electrical shock therapy is the fact that atrial defibrillation shock may lead to ventricular fibrillation. This is because a moderate level shock during the repolarization of the ventricles will typically lead to fibrillation. In order to avoid this problem, the prior art utilizes methods and apparatus to sense the R-wave in the right ventricle and to carefully synchronize the atrial shock to avoid impinging upon the ventricular T-wave which would represent the repolarization of the ventricle. The risk of fibrillating the heart with an atrial defibrillation shock can also be minimized by delivering shocks which are timed with ventricular activity. This method is generally disclosed in U.S. Pat. Nos. 5,207,219; 5,350,402; and 5,411,524.

In spite of the advances made by the prior art, atrial defibrillation shock therapy may cause ventricular fibrillation and therefore therapy for an otherwise non-fatal condition might be fatal to the patient. One possible solution is to incorporate a ventricular defibrillator with an atrial defibrillator. However, the energy required for a ventricular defibrillation is significantly higher than that required for atrial fibrillation. Therefore, the capacitors and batteries needed for ventricular defibrillation are much larger and the device would need to be the same size as a conventional implantable cardiac ventricular defibrillator.

An alternate therapy for atrial defibrillation comprises drug injection devices. Numerous prior art devices disclose various types of implantable drug pumps which discharge an amount of drugs at the onset of atrial fibrillation.

While prior art methods and devices for attempting to stop atrial fibrillation have performed adequately, they continue to suffer from the drawbacks of potentially causing ventricular fibrillation, being large in size, and being very costly.

SUMMARY OF THE INVENTION

As can be seen from the above, there is an acute need for an inexpensive, implantable device that prevents the dangerous side effects of atrial fibrillation without causing ventricular fibrillation. The present invention comprises an apparatus and a method for preventing clots from forming during atrial fibrillation and thus eliminating the dangerous side effects of atrial fibrillation.

The present invention is an implantable device for preventing clotting during atrial fibrillation. The device of the present invention includes electrical cardiac output forcing (ECOF) back up. The device includes a power supply for operating the device and for providing the necessary output forcing signals. The power supply is located in a housing which is implantable into a human patient, although various embodiments may comprise external power supply means. In a preferred embodiment of the present invention, the housing acts as an electrode. At least one additional electrode is connected to the housing and is insertable into the human heart. A ventricular lead is mounted to the electrode as is an atrial lead. The housing also contains an electrical cardiac output forcing stimulator. When atrial fibrillation is detected, anti-clotting pulses are applied to the heart via the atrial lead. If and when ventricular fibrillation is detected, ECOF pulses or ICD shock pulse(s) are applied to the heart via the ventricular lead. Additionally, in the preferred embodiment of the present invention, the anti-clotting pulses are synchronized to the R-wave sensed by the ventricular lead.

DETAILED DESCRIPTION OF THE PREFERRED EMBODIMENT

The present invention comprises an implantable device for preventing clotting during atrial fibrillation. The device of the present invention also includes electrical cardiac output forcing (ECOF) back up or ICD back up.

Figure 1:
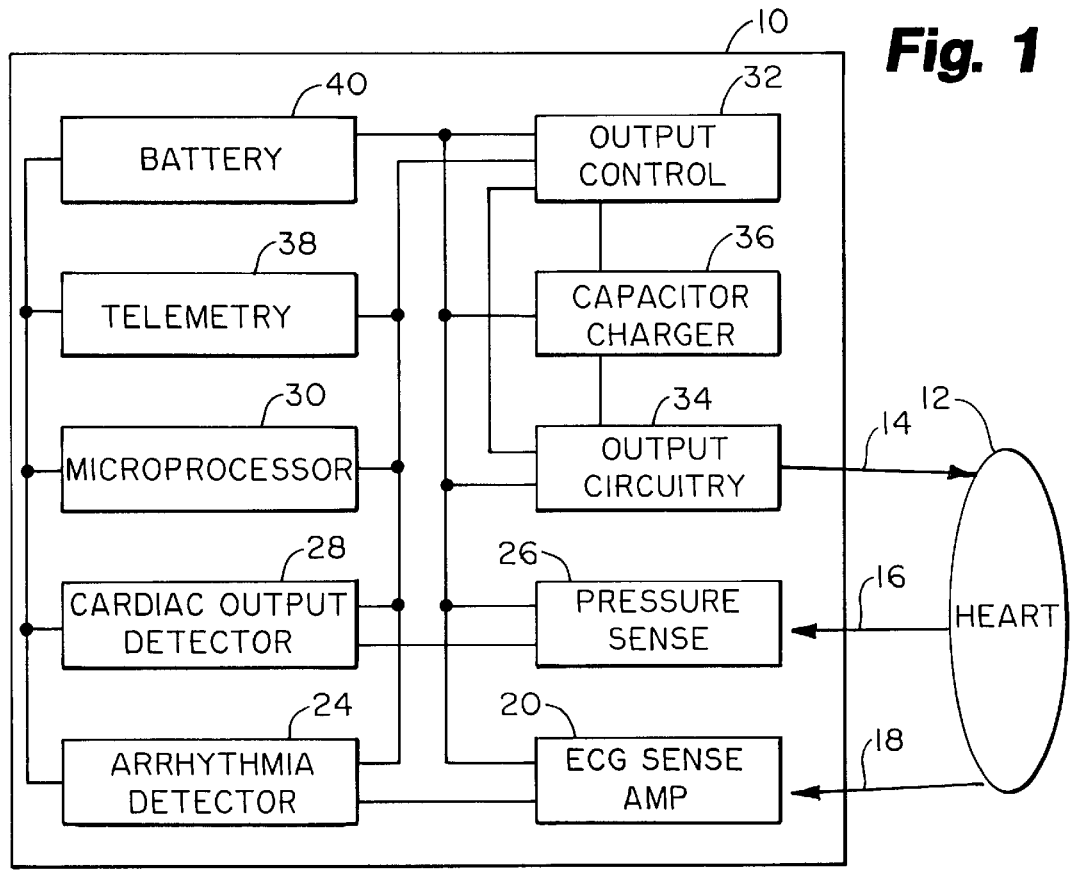
FIG. 1 is a block diagram illustrating a system constructed in accordance with the present invention.

FIG. 1 illustrates a block diagram of a system constructed in accordance with the present invention. System 10 is connected to a heart 12 by a series of leads including an output lead 14, an optional pressure sensing lead 16, and an ECG sensing lead 18. System 10 includes a conventional ECG amplifier 20 for amplifying cardiac signals. The amplified cardiac signals are analyzed by a conventional arrhythmia detector 24 which determines if a dysrhythmia (e.g., an arrhythmia) is present. System 10 also contains optional pressure sensing section 26 which amplifies and conditions a signal from an optional pressure sensor within heart 12. The output of pressure sensor circuit 26 is fed to a cardiac output detection circuit 28 which analyzes the data and determines an estimate of cardiac output. Data from arrhythmia detector 24 and cardiac output circuit 28 is fed to a microprocessor 30. Microprocessor 30 determines if electrical cardiac output forcing (ECOF) pulses having a first voltage type and/or a shock-type of pulses having a second voltage type are appropriate. If forcing is indicated, microprocessor 30 prompts an output control 32 to charge a capacitor within an output circuitry 34 via a capacitor charger 36. Output control 32 directs output circuitry 34 to deliver pulses to heart 12 via output leads 14. Additionally, microprocessor 30 may communicate with external sources via a telemetry circuit 38 functionally encompassed within system 10. The power for system 10 is supplied by an internal power means, such as battery 40.

Figure 2:
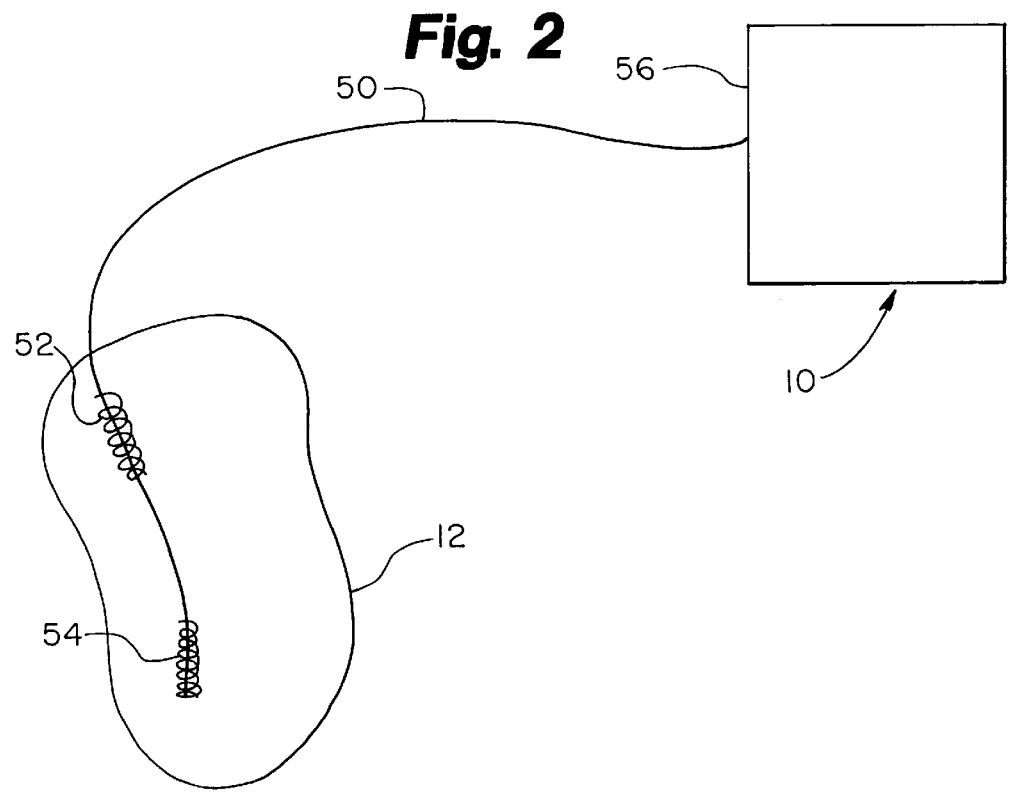
FIG. 2 is a perspective view of the system of the present invention in an endocardial lead configuration.

FIG. 2 illustrates a non-thoracotomy configuration for the present invention. As can be seen, an electrode 50 is connected to system 10 and inserted into heart 12. An atrial lead 52 is positioned in the atrium for providing anti-clotting pulses. A ventricular lead 54 is positioned in the ventricle for sensing R-waves for synchronization of the anti-clotting pulses and for providing back up ECOF or ICD functionality. System 10 is provided with housing 56. Housing 56 acts, in one embodiment, as an electrode such that current flow is from leads 52 and 54 to housing 56.

With the present invention, when atrial fibrillation is detected by arrhythmia detector 24, system 10 supplies low voltage "ECOF" pulses in the range of about 10–100 volts to an atrium via output lead 14. This will force cardiac output of the atrium and prevent blood clots from forming.

If ventricular fibrillation is sensed by arrhythmia detector circuit 24, said first voltage type of ECOF pulses will be delivered to the heart to maintain life until external defibrillation therapy is administered. Alternatively, if ventricular fibrillation is sensed by arrhythmia detector 24, said second type of voltage type may be delivered to the heart. This second type of voltage will typically be of a voltage value greater than said first type and similar to that voltage normally attributable to I.C.D. shock-type voltages.

As stated above, the goal of ECOF is maintaining some cardiac output yet not necessarily defibrillation. Similarly, the goal of the anti-clotting pulses is to prevent clotting while not necessarily stopping the atrial fibrillation. It is possible, and in fact beneficial, if the anti-clotting pulses stopped atrial fibrillation and if the ECOF pulses stopped ventricular fibrillation, but it is not the main purpose of either type of pulses. To accomplish the goals of the anti-clotting and ECOF pulses, a forcing field is generated by applying approximately 50 V to the heart at a rate of approximately 100–180 beats per minute. These fields are applied after detection of an arrhythmia and maintained for a predetermined time period. The application of the forcing fields will generate a cardiac output which is a fraction of the normal maximum capacity. The heart has a four or five times reserved capacity so this fraction of the normal pumping activity will prevent clotting in the case of atrial fibrillation and will maintain life and consciousness to allow a patient enough time to get to a hospital in the case of ventricular fibrillation. In the case of ventricular fibrillation, the patient would then be a candidate for an implantable cardioverter defibrillator.

Figure 3:
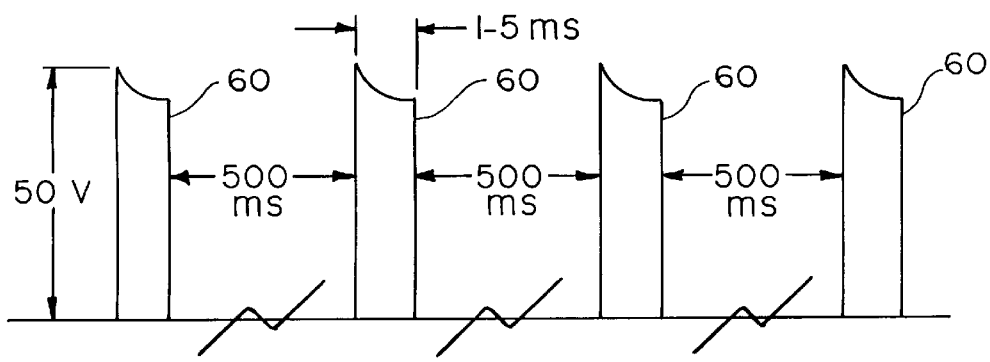
FIG. 3 illustrates a representative electrical signal of the present invention.

A series of forcing pulses 60 are shown in FIG. 3. The pulses are approximately 50 V in amplitude with a spacing of approximately 500 ms. The 50 V and 500 ms pulse spacing are chosen as merely illustrative for an implantable device. The forcing pulse interval is chosen to maximize cardiac output within the limits of device circuitry and the response of the heart muscle. An interval of 500 ms corresponds to a heart rate of 120 beats per minute. However, a rate of 240 beats per minute would produce a lower output due to mechanical limitations of the heart. Thus, a practical range is 60 to 200 beats per minute. The pulses could also be timed to coincide with the natural pumping of the atria, thus improving overall cardiac output.

The higher the voltage, the higher the forcing fields, and therefore a greater number of heart cells contracting producing greater cardiac output. However, the higher voltage produces greater patient discomfort and extraneous muscle twitching.

Implantable batteries are also limited to a certain power output and energy storage. If an output pulse is 50 V and the electrode impedance is 50 ohms, the power during the pulse is $P = V^2/R = 50$ V/50$\Omega$ = 50 W. If the pulse has a duration of 2 ms then the energy per pulse is 0.1 J. If two pulses are delivered every second, the charger must be capable of delivering 0.2 J per second which is 200 mW. This is well within the limits of an implantable battery. An implantable battery can typically deliver 5 W of power. However, 200 V pulses at 3 per second would require 4.8 W which is near the limit of the battery and charging circuitry. A typical implantable battery energy capacity is 10,000 J. Delivering forcing pulses at a rate of 4.8 W would deplete the battery in only 35 minutes (10,000 J/4.8W=2083 seconds). Thirty-five minutes may not be enough time to transport the patient to a hospital. Therefore, 200 V represents the highest practical voltage for continuous operation in an implantable device, although voltages of up to 350 V could be used for short periods and reduced downwardly when hemodynamic output is verified. A practical lower limit is about 10 V. During normal sinus rhythm, a 10 V signal delivered through the electrodes would pace. However, during fibrillation the 10 V signal could not pace and only cells very near the electrodes would be captured. This 10 V signal would be insufficient for forcing cardiac output.

These calculations also suggest other differences between an implantable ECOF and an ICD. With a battery storing 10,000 J and ECOF pulse having 0.1 J, this ECOF would be capable of delivering 100,000 pulses. An ICD can only deliver 200–4300 shocks of about 30 J. The ECOF is also very different from an implantable pacemaker which typically delivers 150,000,000 pacing pulses (5 years at 60 BPM) each of about 0.00005 J.

Figure 4:
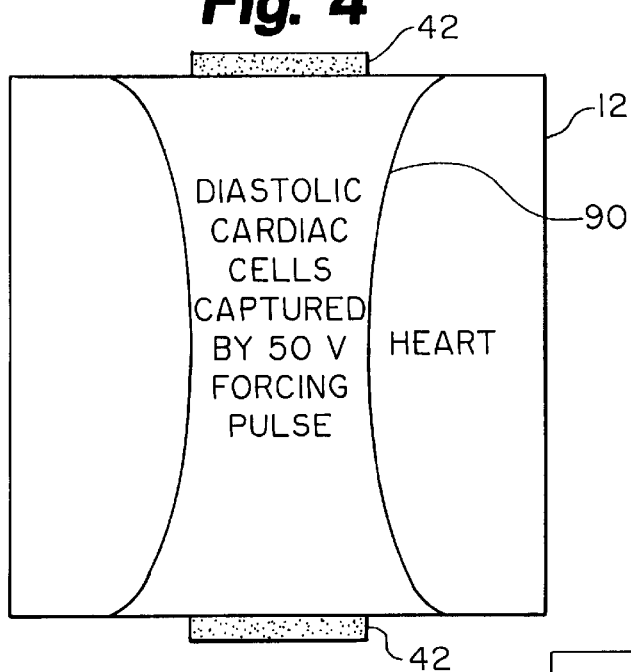
FIG. 4 illustrates the expected effect of a 50 volt pulse on a heart during diastole.

FIG. 4 is a diagram showing the effect of a 50 V forcing pulse of heart 12 during electrical diastole (cells at rest). The current is passed through heart 12 by electrodes 42. Approximately 60% of cardiac cells 90 would be captured by a 50 V pulse if the cells were is diastole. Captured cells 90 mostly lie in the direct path between electrodes 42 and near electrodes 42 where the field strengths are highest. Of course, over a time period of about 100 ms these directly captured cells then propagate an activation wavefront to stimulate the rest of the heart. This so called far-field pacing is irrelevant here as the hearts, of interest, are in fibrillation and not in diastole.

Figure 5:
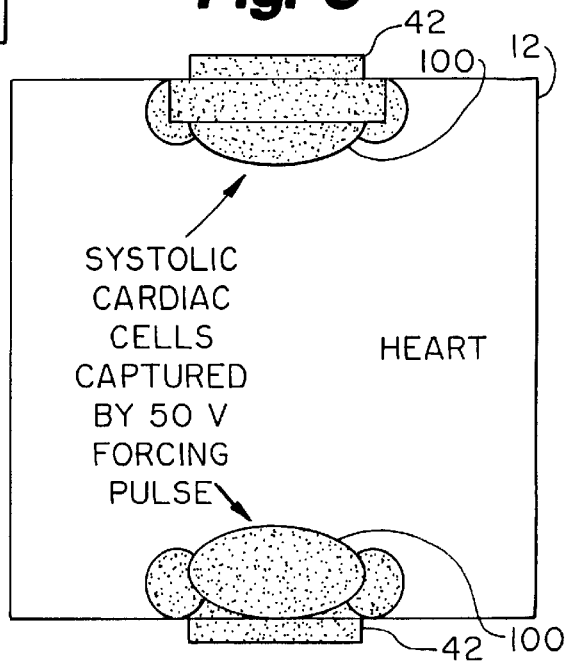
FIG. 5 illustrates the expected effect of a 50 volt pulse on a heart during systole.

FIG. 5 is a diagram showing the effect of a 50 V forcing pulse on the heart during electrical systole (cells already stimulated). The current is passed through heart 12 by electrodes 42. Approximately 20% of cardiac cells 100 would be captured by a 50 V pulse if the cells were in systole. The captured cells 100 are nearest each electrode 42 where the field strengths are highest. Capture in systolic cells means that their activation potential is extended. This capture requires significantly higher fields (10 V/cm) than those required for diastolic cell capture (1 V/cm).

Figure 6:
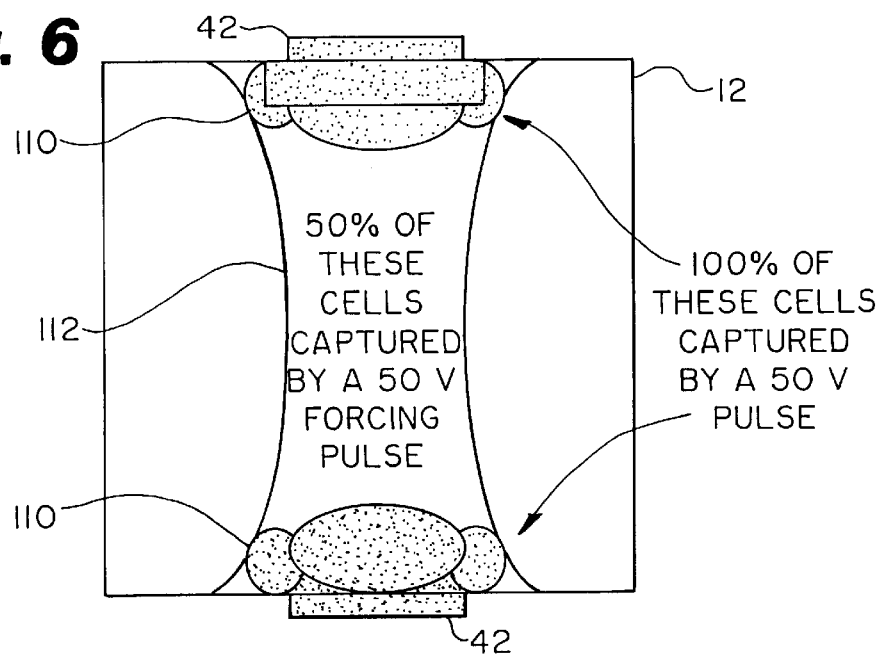
FIG. 6 illustrates the expected effect of a 50 volt pulse on a heart during fibrillation.

FIG. 6 is a diagram showing the effect of a 50 V forcing pulse on the heart during fibrillation. During fibrillation there are always cells in systole and diastole simultaneously. But, the vast majority are in systole. This diagram assumes 50% of the cells are in diastole which applies only after several capturing pulses. The current is passed through heart 12 by electrodes 42. One hundred percent of the cells 110 nearest electrodes 42 would be captured due to the high field strength. As shown in FIG. 5, even systolic cells are captured by high field strengths. Fifty percent of cells 112 in the direct path between electrodes 42 would be captured if it is assumed that 50% of all cells are in diastole. If roughly 60% of cardiac cells are captured by a 50 V pulse when the cells are in diastole, and 20% are captured when in systole, and if 50% are in systole and 50% in diastole, 40% would be captured during fibrillation. This calculation is shown in the following table. The last two columns give the mechanical action resulting and the contribution to forcing a cardiac output. Considering the cardiac cells that are originally in diastole, (rows A & B) in the table below, the A row represents the diastolic cells that are not captured by the forcing pulse. If 50% of the heart's cells are in diastole and 40% of those are not captured that is 20% of the total cells. These cells will, however, shortly contract on their own (from previous wavefronts or new ones) providing a positive gain in mechanical action and therefore cardiac output. The B row corresponds to the diastolic cells that are captured. If 60% of the diastolic cells (50% of total) contract due to the forcing field this is 30% of the total heart cells. These cells provide the biggest gain in mechanical action and cardiac output. Next considering the activity of the systolic cells (rows C & D), if 50% of the heart's cells are in systole and 80% of those are not captured (row C), that is 40% of the heart's cells. These cells soon relax and negate a portion of the cardiac output. The systolic cells that are captured (row D) are 10% of the heart's cells (20% of 50%). These cells will hold their contraction and be neutral to cardiac output. The net result is a gain in contraction which forces cardiac output.

| Original status of the cells | Percentage of the cardiac cells | Status of the cardiac cells | Percentage of the original status | Percentage of the total cells | Mechanical Action | Forcing Cardiac Output Effect |
|---|---|---|---|---|---|---|
| (A) Diastolic | 50% | Diastolic non-captured | 40% of 50% | 20% | will start to contract on own | positive (+) |
| (B) Diastolic | | Diastolic captured | 60% of 50% | 30$ | contract | positive (++) |
| (C) Systolic | 50% | Systolic non-captured | 80% of 50% | 40% | will start to relax on own | negative (−) |
| (D) Systolic | | Systolic captured | 20% of 50% | 10% | hold | neutral (0) |
| Total | 100% | | 100% | 100% | more contraction | positive (++) |

The net result over a 200 ms mechanical response is given in the next table. The major contribution is in row (B) from the captured diastolic cells contracting.

| Row | Status of the Cardiac Cells | Change in Output | Description of Activity |
|---|---|---|---|
| A | Diastolic non-captured | +5% | Positive. Some cells will begin to contract on their own. |

-continued

| Row | Status of the Cardiac Cells | Change in Output | Description of Activity |
|---|---|---|---|
| B | Diastolic captured | +30% | Positive. Cells contract due to forcing field. |
| C | Systolic non-captured | −5% | Negative. Some cells will begin to relax on their own. |
| D | Systolic captured | 0% | Neutral. Cells hold contraction due to forcing field. |
| Net Gain | | +30% | A net gain in cardiac output due to forcing fields. |

The 30% net pumping action should be sufficient to maintain survival and consciousness, because the heart has a 4–5 times reserve capacity.

Figure 7:
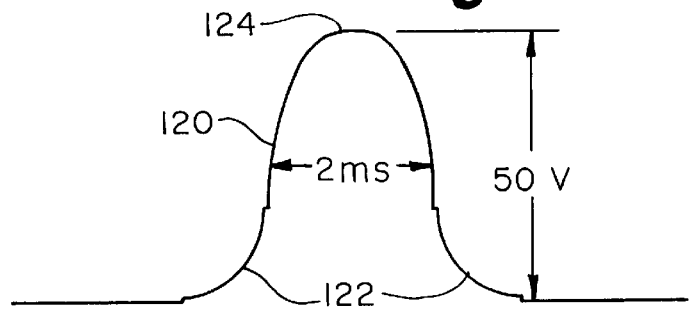
FIG. 7 illustrates a waveform useful for the electrical cardiac output forcing function.
Figure 8:
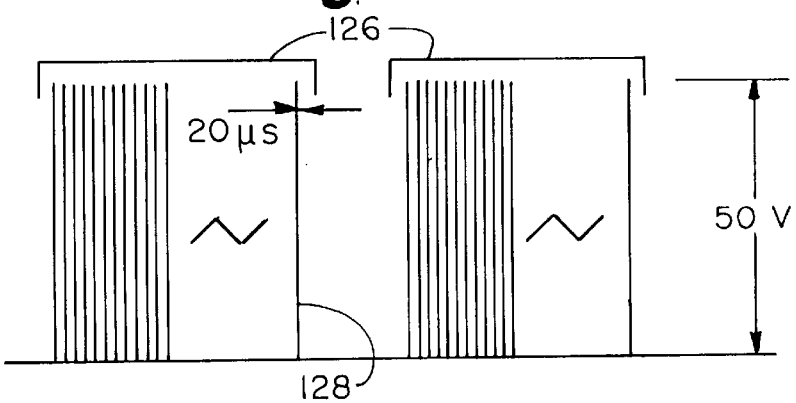
FIG. 8 illustrates an alternative waveform useful for the electrical cardiac output forcing function.

FIGS. 7 and 8 depict examples of waveforms designed to minimize the twitching of the chest muscles which can be very uncomfortable to the patient. In FIG. 7 a low harmonic pulse waveform 120 which has a very gradual "foot" 122 and a gradual peak 124 is illustrated. Such a pulse has less high frequency energy components and thus is less likely to stimulate the skeletal muscle. FIG. 8 shows the opposite extreme. Here, each compound forcing pulse 126 is actually composed of 50 very short spikes 128 each of which is 20 $\mu$s in width with a 20 $\mu$s spacing. The heart will tend to average out these thin pulses and "see" a 2 ms wide forcing pulse. The skeletal muscle, however, is not efficiently stimulated by these extremely narrow pulses. The skeletal muscle will not average out this signal either. This approach could help minimize skeletal muscle twitching and discomfort.

An alternative system would be to initially apply a 300 V pulse to capture many cells therefore putting those cells into diastole after a delay of 100–200 ms. At this point, the voltage could be lowered to 100 V and delivered every 100 ms. A 3 watt DC—DC converter with a 67% efficiency could provide 100 ms interval forcing pulses assuming a 50 ohm resistance and 1 ms pulse (0.2 J). This rate is too fast for forcing cardiac output due to mechanical limitations, but is very effective for electrical capture. After sufficient capture, the rate of forcing pulses could be slowed down to 100–170 beats per minute for optimum cardiac output.

In a preferred embodiment of the present invention, the duration of the anti-clotting pulse will be approximately twenty seconds. If atrial fibrillation is constant, additional low voltage anti-clotting pulses in the range of 10–100 volts will be applied periodically, e.g., approximately every thirty minutes. In order to enhance the effectiveness of the anti-clotting pulses and to prevent ventricular fibrillation these low voltage ECOF pulses for preventing blood clots are synchronized to the ventricular R-wave sensed by ventricular lead 54.

As previously stated, synchronizing the delivery of the anti-clotting pulses to the atria with a ventricular electrical activation (the R-wave) of the heart is important to minimize the possibility of the inducement of ventricular fibrillation. Ventricular fibrillation is much more likely to occur if the anti-clotting pulses are applied during a vulnerable period of the patient's ventricles. An electrocardiogram waveform under normal conditions includes a P-wave, followed by a complex three-part waveform called the QRS pattern, and then a T-wave. The vulnerable period of the patient's ventricles occurs during repolarization of the ventricles which usually begins 30–40 milliseconds before the apex of the T-wave and ends near the apex of the T-wave. The R-wave is the dominant amplitude feature and is therefore most typically used to sense a heart beat. In the present invention, the R-wave is detected by ventricular lead 54.

Figure 9:
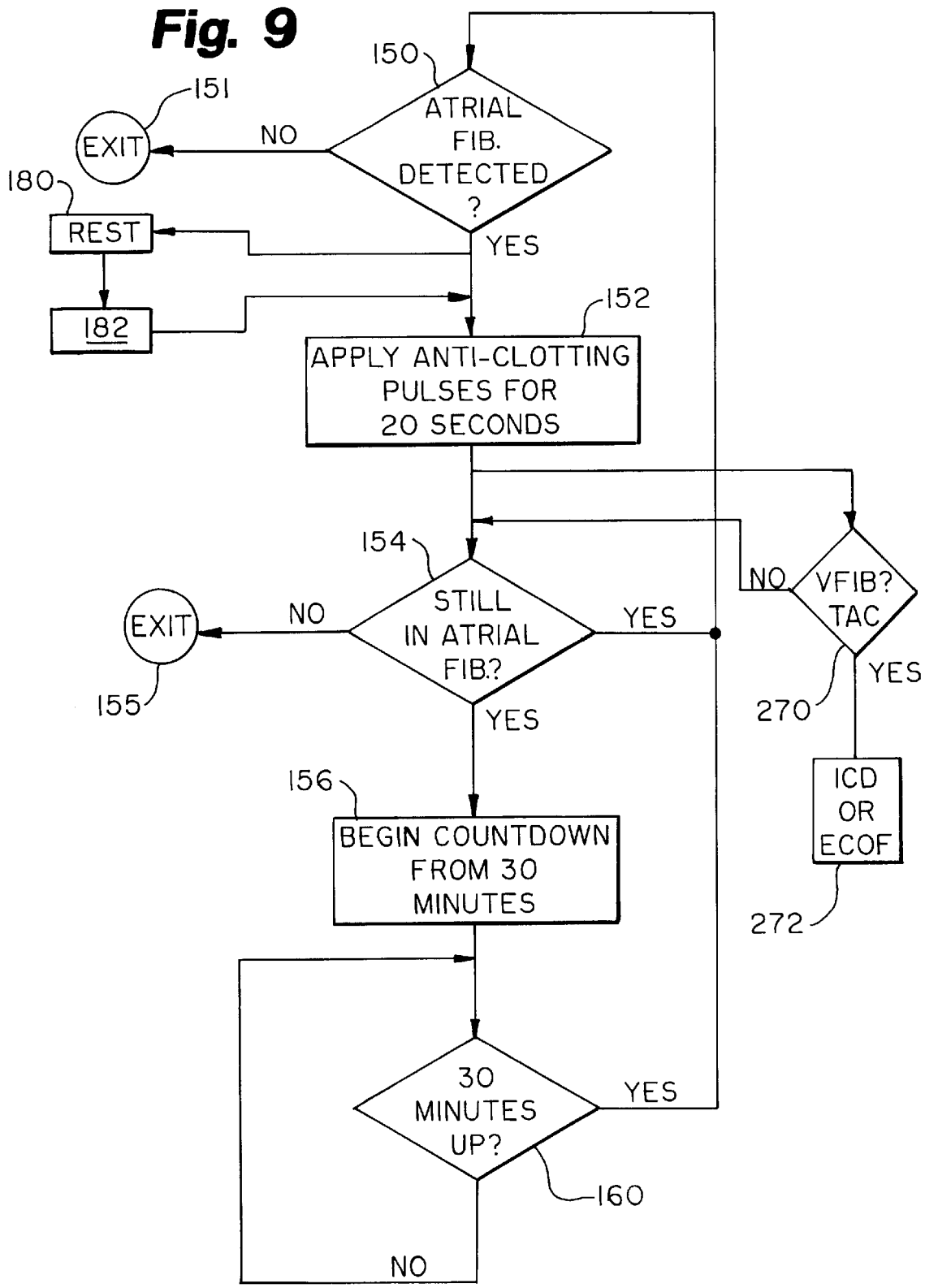
FIG. 9 is flow chart illustrating the anti-clotting pulsing portion of the present invention.

FIG. 9 illustrates a flow chart of the operation of a preferred embodiment of the present invention once atrial fibrillation has been detected. Once atrial fibrillation is detected in block 150, twenty seconds worth of anti-clotting pulses are automatically applied in block 152. If atrial fibrillation is not detected in block 150, the anti-clotting therapy ceases and exits at block 151. After the application of the anti-clotting pulses in block 152, the status of the heart is again determined in block 154. If atrial fibrillation is still present, a thirty minute counter is set in block 156. If the heart is no longer in atrial fibrillation at block 154, the anti-clotting therapy ceases and the routine is exited at block 155. Note that this means that the anti-clotting pulsing has successfully stopped atrial fibrillation of the patient's heart even though this is not a primary goal of the system. After it has been determined that thirty minutes has expired in block 160, the routine returns to block 150 for determination as to whether or not atrial fibrillation is still detected. If atrial fibrillation is still detected, the entire procedure is repeated.

It is recognized that in the above method it is possible to adjust the time periods as appropriate for the patient. Indeed, it is also possible to include additional optional steps 270, 272. In step 270, a determination is made whether the heart is in ventricular fibrillation (or possible ventricular tachycardia according to the patient) and, if such condition does not exist then proceeding to step 154. If the ventricular condition does exist, then step 272 is implemented. In step 272 energy is applied at either an ECOF or ICD voltage level, as appropriate, to facilitate escape from the condition and return of the ventricle to as close to normal rhythm as is possible. The goal, of course, is to provide this form of backup to enhance the value of the anti-clotting method and device while reducing any secondary risk.

A further embodiment is shown in FIG. 9 as optional steps 180, 182. In this embodiment, following detection of atrial fibrillation in step 150, a rest period of no further device activity occurs. During this period, which may vary from minutes to days, certain patient dependent therapy may be implemented as shown in step 182. For example, step 182 may include drug therapy, or other patient dependent means for controlling the atrial fibrillation. However, even if steps 180 and 182 are implemented, or whether those steps are successful, it may still be appropriate to proceed to the anti-clotting pulses of step 152.

Figure 10:
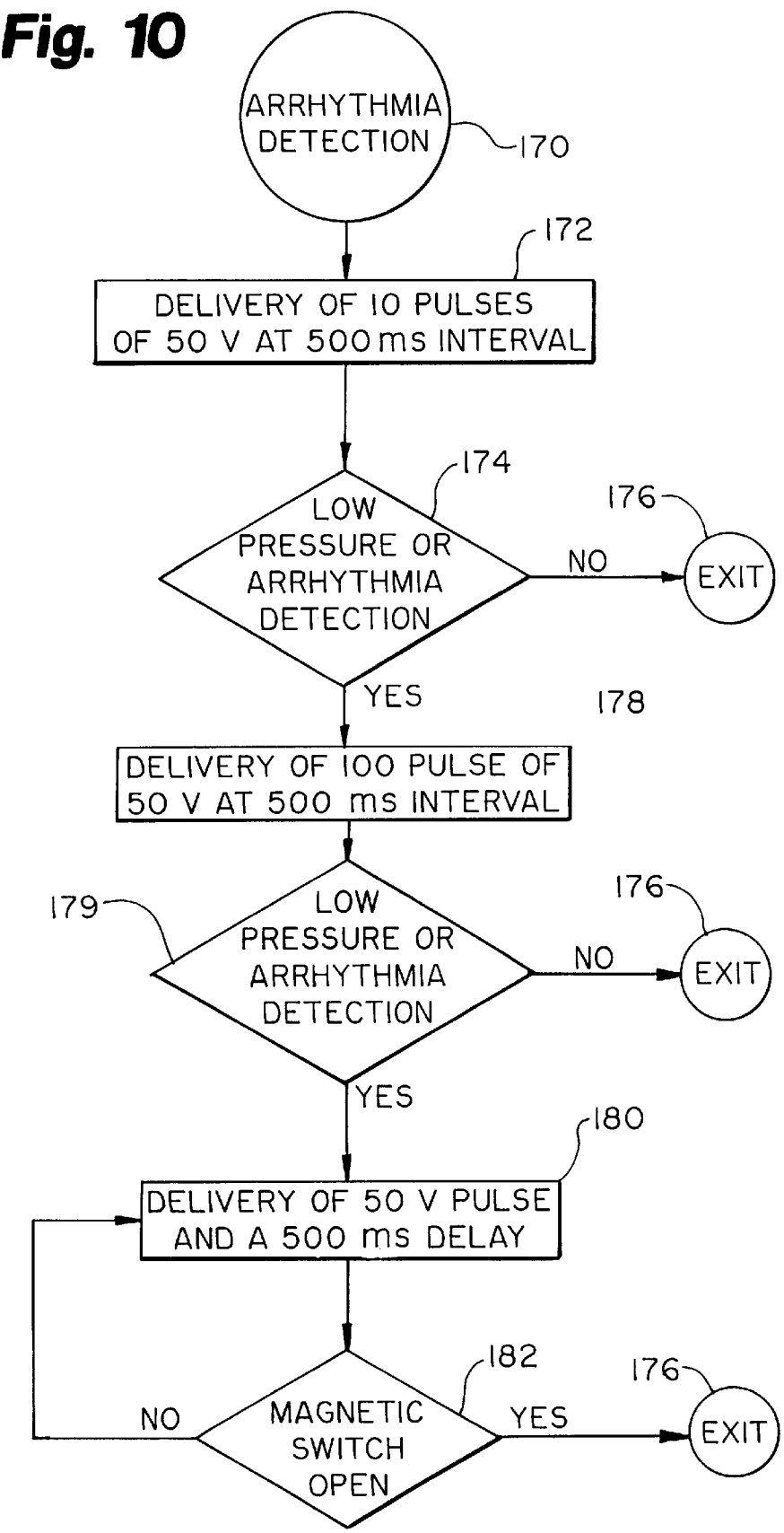
FIG. 10 is a flow chart illustrating the ECOF portion of the present invention.

FIG. 10 is a flow chart illustrating a method of applying ECOF pulses according to the present invention. It should be noted that this chart is provided for purposes of illustration only and that one skilled in the art will recognize from the discussion that alternative methods may be employed without departing from the principles of the invention. The flow chart shown in FIG. 10 represents a method of automatically treating a heart which is in fibrillation, tachycardia, or asystole and thereby pumping inefficiently or not at all. Once an arrhythmia is detected in block 170, a series of cardiac output forcing electric pulses are automatically delivered in block 172. It should be understood that the therapy may be delivered for any output comprising cardiac arrhythmia or dysrhythmia, or other condition likely to promote thrombosis within the heart. Indeed, certain patients may be appropriate candidates for full time or near full time administration of atrial ECOF therapy to facilitate ventricular functioning. In this instance, it may be appropriate to anticipate the R-wave by approximately 100–200 ms. Referring again to FIG. 10, after delivery of ten forcing pulses (at a rate of 60–200 BPM) in block 172, the status of the heart is determined in block 174. If an arrhythmia is still present and there exists low pressure within the heart, more forcing pulses are delivered in block 178. If the heart is pumping at a safe level, the therapy ceases and exits at block 176. Note that this means that the ECOF successfully defibrillated the patient's heart even though this is not a primary goal of the system. For those patients who are defibrillated by ECOF pulse therapy, it is possible they could then receive ECOFs instead of the larger ICD, although as noted above, a hybrid approach is also possible.

After the therapy in block 178 has been delivered, the pressure and ECG is again monitored in block 179. If the therapy is successful, it ceases and exits in block 176. If the therapy from block 178 is unsuccessful in producing a safe level of pumping efficiency, the method proceeds to a continuous cardiac assist mode as in block 180. This therapy may only be stopped by an external command, for example, a telemetry signal or a magnet which is applied to the chest activating a magnetic reed switch as indicated in block 182 which terminates the therapy and exits in block 176. To minimize patient discomfort and maximize battery life, the forcing voltage could be adjusted down when sufficient pressure signals or adequate flow measured by other means were detected, for example, the pressure sense transducer could be replaced by an oxygen detector or a doppler flow measuring device. The pulse rate could also be adjusted to maximize output.

It should be understood that various alternatives to the embodiments of the invention described herein may be employed in practicing the invention. For example, while most of the discussion is in the context of an implantable device, the concepts of the invention are also applicable to external delivery systems. It is intended that the following claims define the scope of the invention and that structures and methods within the scope of these claims and their equivalents be covered thereby.

What is claimed is:

1. An implantable device for preventing clotting during atrial fibrillation comprising:
   an implantable housing;
   at least one electrode connected to the housing;
   an atrial lead mounted to the at least one electrode; and
   a cardiac stimulator in the housing electrically connected to the atrial lead through the at least one electrode wherein the atrial lead applies anti-clotting pulses upon the occurrence of atrial fibrillation.

2. The device of claim 1 further comprising a ventricular lead mounted to the at least one electrode.

3. The device of claim 2 in which said cardiac stimulator is connected to both the atrial lead and the ventricular lead.

4. The device of claim 1 in which the housing forms an electrode.

5. The device of claim 3 in which the atrial lead and ventricular lead further comprise at least one ECG sensor.

6. The device of claim 1, further comprising a control circuit in the housing electrically connected to the at least one electrode, wherein the control circuit applies the anti-clotting pulses in synchronization with a sensed R-wave of the patient's heart.

7. The device of claim 1 in which the anti-clotting pulses are between 10 and 100 Volts.

8. The device of claim 1 in which ECOF pulses are applied to the ventricular lead upon the occurrence of ventricular fibrillation.

9. The device of claim 1 in which at least one ICD shock pulse is applied to the ventricular lead upon the occurrence of ventricular fibrillation.

10. A device for preventing thrombogenic cardiac events in a human and for simultaneously protecting against life threatening effects of possible ventricular rhythm abnormalities, comprising:
    an ECG detector for detecting both atrial and ventricular fibrillation; and
    an electrical cardiac stimulator connected to the ECG detector and configured for producing anti-clotting pulses deliverable to the atrium upon the occurrence of at least one potentially thrombogenic cardiac event and for producing cardiac output forcing signals upon the occurrence of ventricular fibrillation.

11. The device of claim 10 in which the ECG detector detects R-waves of the patient's heart.

12. The device of claim 10 in which the anti-clotting pulses and the cardiac output forcing signals are greater than about 10 volts and less than a normal ICD shock voltage.

13. The device of claim 10 in which the cardiac output forcing signals are at a voltage level of a normal ICD shock.

14. The device of claim 10 in which the anti-clotting pulses are configured for delivery to the atrium of the patient's heart in synchronization with a detected portion of an electrocardiogram.

15. A device for preventing clotting during atrial fibrillation comprising:
    power supply means;
    detection means connected to the power supply means;
    output control means connected to the detection means and to the power supply means for delivering anti-clotting pulses to the atrium of the patient's heart upon the detection of atrial fibrillation and for delivering cardiac therapy signals to a ventricle of the patient's heart upon the detection of ventricular fibrillation.

16. The device of claim 15 in which the detection means comprises an ECG sensor.

17. The device of claim 15 further comprising electrode means for delivering said pulses and signals to the atrium and the ventricle.

18. The device of claim 15 in which the anti-clotting pulses and the cardiac therapy signals are greater than about 10 volts and less than a normal ICD shock voltage.

19. The device of claim 15 in which the cardiac therapy signals are at a voltage level of a normal ICD shock.

20. A method of preventing clotting during atrial fibrillation comprising the steps of:
    a) monitoring the cardiac rhythm of a patient's heart; and
    b) applying anti-clotting electrical pulses to an atrium of the patient's heart upon the detection of a first predetermined cardiac event.

21. The method of claim 20 further comprising the step of applying a cardiac therapy signal to the heart upon the detection of a second predetermined cardiac event.

22. The method of claim 20 in which the first predetermined cardiac event is atrial fibrillation.

23. The method of claim 20 in which the first predetermined cardiac event is the occurrence of at least one potentially thrombogenic cardiac event.

24. The method of claim 21 in which the second predetermined cardiac event is ventricular fibrillation.

25. The method of claim 21, further comprising the step of synchronizing the anti-clotting pulses to the R-wave of the QRS complex of the patient's heart.

26. The method of claim 21 in which the duration of the anti-clotting pulses is determined according to the cardiac needs of each user of the method.

27. The method of claim 21 in which the anti-clotting pulses are applied for a duration of between about 5 seconds and about 60 seconds.

28. The method of claim 21 in which a time period between a plurality of successive anti-clotting pulses is selected between about 1 hour and about 72 hours for users of the method having chronic atrial fibrillation.

29. A method for preventing cardiac thrombogenesis resulting from atrial disrhythmia, comprising the steps of:

a) monitoring the atrial rate of a patient's heart;

b) comparing the atrial rate to a threshold value to detect atrial fibrillation;

c) delivering anti-clotting electrical pulses to an atrium of the patient's heart when the threshold atrial rate is exceeded.

30. The method of claim 29, further comprising the step of monitoring the atrial rate after delivery of the anti-clotting electrical pulses, and if the atrial rate continues to exceed the threshold value then to re-apply the anti-clotting electrical pulses.

31. The method of claim 29, further comprising the step of monitoring the ventricular rate of the patient's heart, and comparing the monitored rate to a threshold rate to determine whether the threshold rate is exceeded by the monitored rate, and if the threshold rate is exceeded then delivering a cardiac therapy electrical signal to the heart.

32. The method of claim 29 in which the step including delivery of cardiac therapy comprises delivery of at least one signal having a voltage greater than a normal pacing voltage so that the ventricular rate is modified to be less than the initial monitored rate after delivery of the cardiac therapy electrical signal.

* * * * *